US00PP09799P

United States Patent [19]

Saville

[11] Patent Number: Plant 9,799

[45] Date of Patent: Feb. 11, 1997

[54] MINIATURE ROSE PLANT NAMED 'SAVASPARK'

[75] Inventor: F. Harmon Saville, Newburyport, Mass.

[73] Assignee: Nor'East Miniature Roses, Inc., Rowley, Mass.

[21] Appl. No.: 593,814

[22] Filed: Jan. 30, 1996

[51] Int. Cl.[6] ..... H01H 5/00

[52] U.S. Cl. ..... Plt./10

[58] Field of Search ..... Plt./10, 28, 29

[56] References Cited

U.S. PATENT DOCUMENTS

P.P. 7,417 1/1991 Hardgrove ..... Plt./10
P.P. 9,507 4/1996 Saville ..... Plt./10

*Primary Examiner*—Howard J. Locker
*Attorney, Agent, or Firm*—Christie, Parker & Hale, LLP

[57] ABSTRACT

A new miniature rose with red flowers of good form.

1 Drawing Sheet

SUMMARY OF THE INVENTION

The present invention relates to a new and distinct variety of rose plant of the miniature rose class, which was created by me by crossing as seed parent an undisseminated seedling of my creation and as pollen parent the variety known as 'Ruimired' (U.S. Plant Pat. No. 5,770). The varietal denomination of this new rose is 'Savaspark'.

Among the novel characteristics possessed by this new variety which distinguishes it from its parents and all other varieties of which I am aware is its attractive red flowers of good form which open well and are borne on a vigorous, profusely blooming plant.

Asexual reproduction by propagation of cuttings of the new variety as performed in Essex County, Mass. shows that the foregoing and other distinguishing characteristics come true to form and are established and transmitted through succeeding propagations.

COMPARISON WITH PARENTS

The new variety produces red flowers larger than its pollen parent and differs from the seed parent in flower color; the seed parent providing orange red flowers.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:
*Seed parent.*—Unnamed seedling.
*Pollen parent.*—'Ruimired'.
Class: Miniature.

The following observations are made of specimens grown under glass in Essex County, Mass., during August and September.

FLOWER

Blooming habit: Continuous.

A. Bud:
(1) *Size.*—About ⅜" long.
(2) *Form.*—Oval, pointed at apex.
(3) *Color.*—As sepals divide, bud color is near 45A.
(4) *Sepals.*—Two of the outer sepals have slight foliation along each edge, one has slight foliation on only one edge and fine serration on the other, the two inner sepals are finely serrated on both sides, usually as long again as the bud. Color near 144A. As flower begins to open, the sepals gradually bend back but do not reach the flower stem until the petals start to fade. The sepals remain attached after the petals drop. The tips usually curl up slightly.
(5) *Peduncle.*—Length generally about 1½ inch, but varying from about 1 inch to 1¾ inch. Aspect, straight. Strength, erect. Color near 144B to 144C.

B. Bloom:
(1) *Size.*—Average size when fully expanded is up to about 1⅜ inch.
(2) *Borne.*—Usually in sprays, but sometimes singly; accompanying illustration shows one stem from the plant; profuse.
(3) *Form.*—High centered, remaining high centered until petals drop from the plant.
(4) *Petalage.*—Number of petals under normal conditions about 18–24.
(5) *Color.*—During first two days, inner petals at center of flower near 45B; reverse near 46C; outer petals near 46B, reverse near 45D; base of petals at point of attachment near 4C; general tonality from a distance medium red.
(6) *Color change.*—As bloom ages, color changes from near 45A to near 45B and near 46B, to near 45D and near 46C, to near 43A to near 47B as the petals drop; general tonality; medium red, after three or more days, medium red.

C. Petals:
(1) *Texture.*—Average for class.
(2) *Appearance.*—Inside velvety and outside satiny.
(3) *Form.*—Obtuse.

(4) *Arrangement.*—Imbricated, regularly arranged, shingle-like.
(5) *Petaloids in center.*—0–3; no distinguishing characteristics.
(6) *Persistence.*—About 8–12 days.
(7) *Fragrance.*—None.
(8) *Lasting quality.*—About 8–12 days on the plant; about 8–15 days as a cut flower, depending on conditions.

REPRODUCTIVE ORGANS

A. Stamens, filaments and anthers:
*Arrangement.*—Regularly arranged around styles at the upper/outer edge of the receptacle.
B. Stamens:
*Quantity.*—About 30–40.
C. Filaments:
*Approximate length.*—About 7/32 inches.
*General Color.*—Near 6C at the base to near 42D just below the anther.
D. Anthers:
*Color.*—Near 21C.
E. Pollen
*Color.*—Near 26A.
*Quantity.*—Very small amount.
F. Pistils:
*Quantity.*—Average for the small flower size.
G. Styles: Uneven length up to about 3/16", and only varying in length by about 1/16".
*Color.*—Near 4A at their base to near 53D just below the stigma.
H. Stigmas:
*Color.*—Near 4A.
I. Hips:
*Shape.*—Globular to bowl shaped.
*Size.*—Up to about 15/32".
*Color.*—May be near 32A and 33A to near 30B.

PLANT

A. Form: Upright.
B. Growth: Very vigorous, uniform branching.
*Height.*—About 20–26".
*Spread.*—Up to about 24" wide.
*Length of flowering stem.*—Varying greatly, depending from where it originates. They have been measured from 5" up to 14" long, ending in a single flower of a spray.
C. Foliage: Compound of 5 leaflets and occasionally 3 or 7 leaflets.
*Size.*—Small.
*Quantity.*—Abundant.
*Color.*—New foliage: Upper side near 146B; under side near 147C, may be flushed with 183B. Old foliage: Upper side near 137B; under side near 138B.
*Shape.*—Leaflet oval pointed.
*Texture.*—Upper side semi-glossy; underside matte.
*Thorns, prickles or hairs.*—Varying amounts of prickles on underside of leaf stem.
*Edge.*—Serrated.
*Serration.*—Very fine and even.
*Leaf stem.*—Color near 146C; underside near 144B.
*Stipules.*—Finely bearded.
*Resistance to Diseases.*—Blackspot: Good. Mildew: Good. Rust: Good.
D. Wood:
*New wood.*—Color near 147B; bark smooth
*Old wood.*—Color toward light, near 177A, otherwise near 146A; bark smooth.
E. Thorns:
*Quantity.*—On main stalks from base is ordinary; usually 1 to 3 per inch of stalk length on laterals from stalk.
*Length.*—Small up to about 1/4".
*Color.*—Near 187A.
*Position.*—Irregular.
F. Prickles:
*Main stalk.*—None.
*Laterals.*—None.
*Leaves.*—Usually 1 to 6 prickles on underside of leaf stems.
G. Winter hardiness: Needs protection in severe climate.

I claim:

1. A new and distinct variety of rose plant of the miniature rose class, substantially as shown and described.

* * * * *

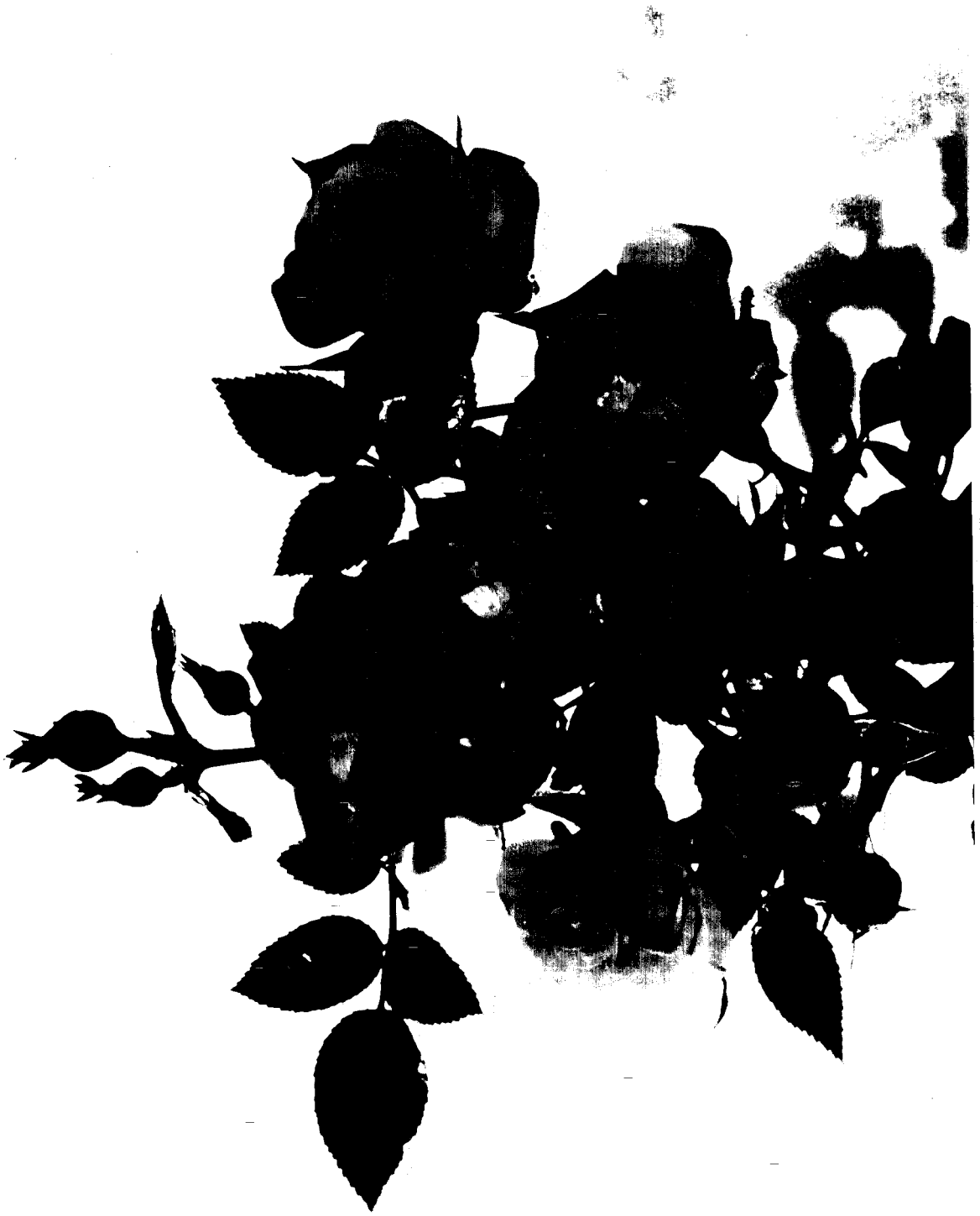

UNITED STATES PATENT AND TRADEMARK OFFICE

CERTIFICATE OF CORRECTION

PATENT NO. : Plant 9,799
DATED : February 11, 1997
INVENTOR(S) : F. Harmon Saville It is certified that error appears in the above-indentified patent and that said Letters Patent is hereby corrected as shown below:

Column 4, line 4, after "flower" change "of" to -- or --.
Column 4, line 32, replace "187A" with -- 178A --.

Signed and Sealed this

Twenty-eighth Day of October, 1997

*Attest:*

Bruce Lehman

BRUCE LEHMAN

*Attesting Officer*

*Commissioner of Patents and Trademarks*